(12) United States Patent
Ip et al.

(10) Patent No.: US 7,022,670 B1
(45) Date of Patent: Apr. 4, 2006

(54) NEUROTROPHIN NT-7 FROM CARP

(75) Inventors: Nancy Yuk-Yu Ip, Hong Kong (HK); Kwok On Lai, Wan Chai (HK)

(73) Assignee: Hong Kong University of Science & Technology, Kowloon (HK)

( * ) Notice: Subject to any disclaimer, the term of this patent is extended or adjusted under 35 U.S.C. 154(b) by 0 days.

(21) Appl. No.: 09/157,984

(22) Filed: Sep. 22, 1998

(51) Int. Cl.
*C07K 14/475* (2006.01)
*A61K 38/18* (2006.01)

(52) U.S. Cl. .......................................... 514/12; 530/399
(58) Field of Classification Search ................ 536/350, 536/399; 514/12
See application file for complete search history.

(56) References Cited

OTHER PUBLICATIONS

Lai et al. Mol. Cell. Neurosci. 11:64-76, 1998.*
Nisson et al. FEB Lett. 424:285-290, 1998.*
Gotz, Rudolf et al, "Neurotrophin-6 is a new member of the nerve growth factor family", Nature, vol. 372, Nov. 17, 1994, pps. 266-269.

* cited by examiner

*Primary Examiner*—Robert C. Hayes
(74) *Attorney, Agent, or Firm*—Baker & McKenzie LLP

(57) ABSTRACT

A purified neurotrophin, NT-7, including nucleic acid sequences encoding neurotrophin-7 isolated from Cyprinus carpio (carp) is described along with compositions derived therefrom.

2 Claims, No Drawings

NEUROTROPHIN NT-7 FROM CARP

FIELD OF INVENTION

The invention relates to a novel neurotrophin called NT-7. NT-7 possesses structural characteristics of the family of neuroactive proteins called neurotrophins. NT-7 has been found to support the survival and neurile outgrowth of embryonic chick dorsal root ganglion neurons and has been found to activate the receptor tyrosine kinase, Trks.

BACKGROUND

A new stage of development begins with the formation of synaptic contacts between growing axons and their synaptic partners. Once these synaptic contacts are made, the neurons are partly dependent on the presence of their partners for continued survival and differentiation. In the absence of the synaptic targets the axons and dendrites of developing neurons atrophy and the nerve cells may die. The long-term dependency between neurons and their target is called trophic interaction. Neurotrophic factors are signalling molecules provided to neurons by trophic interaction. Neurotrophic factors originate from target tissues and regulate neuronal survival and subsequent growth and differentiation. The two major functions of neurotrophic signalling are the survival of a subset of neurons from a considerably larger population, and the formation of appropriate numbers of connections. The current neurotrophic hypothesis makes a number of assumptions about neurons and their targets. First, neurons depend on the availability of a minimum concentration of trophic factor for survival and subsequently for the persistence of their target connections. Secondly, target tissues synthesise and make available to developing neurons appropriate trophic factors. Third, targets produce trophic factors in limited amounts. Consequently the survival of developing neurons (and later, the persistence of neuronal connections) depends upon neuronal competition for available neurotrophic factor. It is now known that neurotrophins are a family of related trophic proteins. This family consists of four members in mammals that share high homology to each other (about 50% amino acid identity).

The first identified neurotrophic factor, nerve growth factor (NGF) mediates cell survival among two specific neuronal populations in birds and mammals (sympathetic and a sub-population of sensory ganglion cells). Research has shown the death of the relevant neurons in the absence of NGF, survival of a surplus of neurons in the presence of elevated levels of factor; the presence and production of NGF in neuronal targets; and the existence of receptors for NGF in innervating nerve terminals. These observations now define the criteria that must be satisfied to conclude that a factor is a neurotrophin.

Other known members of the neurotrophin family include brain-derived neurotrophic factor (BDNF), neurotrophin-3 (NT-3), and NT-4/5. Another neurotrophin, NT-6 has been discovered from the platfish Xiphophorus maculatus and Xiphoporus Lellen (Gotz et al, 1994).

Neurotrophins bind to two classes of receptors: the p75 receptor binds to neurotrophic with low affinity whilst higher affinity binding is observed with a family of receptor tyrosine kinases called Trks. This family of receptors currently contains three proteins designated TrkA, TrkB and TrkC.

The expression of a particular Trk receptor confers on the neuron the capacity to respond to the corresponding neurotrophin. Also, since neurotrophins and Trk receptors are expressed only in certain cell types in the nervous system, the binding between the neurotrophic factor and receptor accounts for the specificity of neurotrophic interactions.

Binding of neurotrophic factors to their specific receptors result in the phosphorylation of the Trk receptor.

NGF specifically activates TrkA, BDNF and NT-4/5 interact with TrkB whilst NT-3 preferentially activates TrkC.

All the neurotrophins are basic proteins of about 120 amino acids being processed from larger precursors. There are some structural features common to all members of the neurotrophin family. These include encoding of the whole precursor protein in a single exon, the basic amino acids at the end of the pre-pro region that are important in proteolytic cleavage during processing of the precursor molecule, and the presence of six cysteine residues that are thought to maintain three-dimensional conformation of the molecule by disulfide bond formation. Moreover, there are conserved regions, mainly around the cysteine residues, that contain similar amino acid sequences in all neurotrophins. Taken together, these structural features define useful criteria in the identification of novel neurotrophins.

Alignment of amino acid sequence with other neurotrophins suggests that NT6 is structurally more related to NGF. However, NT-6 contains an additional feature not shared by all other known neurotrophins: an insertion of 22 amino acids between the second and third cysteine residues of the mature molecule which contains the heparin-binding domain. Although NT-6 is able to support the survival of chick sympathetic and dorsal root ganglion neurons, its potency is much lower than that of mouse NGF, probably reflecting low conservation of the molecule during evolution.

It is an object of the invention to provide a novel neurotrophin.

SUMMARY OF INVENTION

The invention provides an essentially purified neurotrophin, NT-7 having neurotrophic activity and an amino acid sequence SEQ ID NO.:1 as follows:

Lys Ala Asn Asp Phe Leu His Arg Gly Glu Tyr Ser Val Cys
Asp Ser Glu Glu His Trp Val Gly Asn Leu Thr Gln Ala Thr
Asp Leu Arg Gly Asn Glu Val Thr Val Leu Pro His Val Arg
Ile Asn Asn Val Val Lys Lys Gin Met Phe Tyr Glu Thr Thr
Cys Arg Val Ser Lys Pro Ile Gly Ala Pro Lys Pro Gly Gln
Gly Val Ser Gly Val Lys Ala Gly Thr Ser Ser Cys Arg Gly
Ile Asp Asn Glu His Trp Asn Ser Tyr Cys Thr Asn Val His
Thr Phe Val Arg Ala Leu Thr Ser Tyr Lys Asn Gln Ile Ala
Trp Arg Phe Ile Arg Ile Asn Ala Ala Cys Val Cys Val Leu Ser
Arg Asn Ser Trp Arg His or functional variants, analogues and functional fragments of NT-7.

The invention also provides a nucleic acid sequence SEQ ID NO.:2:

AAGGCCAACGACTTCTTGCATCGCGGC-
GAGTACTCTGTGTGTGACAGCGAAGA
GCACTGGGTTGGCAACCTGACCCAAGC-
CACAGACTTACGGGGCAATGAAGTCA CGGTGCT-
GCCACATGTTCGCATCAACAACGTGGT-
GAAGAAGCAGATGTTCTAC
GAGACCACGTGCCGTGTGTCGAAGC-
CCATCGGGGCCCCCAAGCCGGGTCAAG
CAGCGGCGTTAAAGCAGGAAC- GAGT-
CTCTAGCTGTCGTGGGATCGACAACGAG
CACTGGAACTCTTATTGCACCAACGTG-

CACACCTTTGTGCGGGCGTTAACGTCC
TACAAAAACCAGATTGCCTGGAGGT-
TCATCCGAATCAACGCCGCTTGCGTGTG CGTCCT-
CAGCCGCAACTCATGGAGGCAT said nucleic sequence including degenerate versions of the sequence and including nucleic acid sequences that hybridise under stringent conditions to said nucleic acid sequences and encode NT-7.

The invention also provides a composition comprising an essentially purified neurotrophin, NT-7 having neurotrophic activity and an amino acid sequence SEQ ID NO.:1 as follows:

Lys Ala Asn Asp Phe Leu His Arg Gly Glu Tyr Ser Val Cys
Asp Ser Glu Glu His Trp Val Gly Asn Leu Thr Gln Ala Thr
Asp Leu Arg Gly Asn Glu Val Thr Val Leu Pro His Val Arg
Ile Asn Asn Val Val Lys Lys Gln Met Phe Tyr Glu Thr Thr
Cys Arg Val Ser Lys Pro Ile Gly Ala Pro Lys Pro Gly Gln
Gly Val Ser Gly Val Lys Ala Gly Thr Ser Ser Cys Arg Gly
Ile Asp Asn Glu His Trp Asn Ser Tyr Cys Thr Asn Val His
Thr Phe Val Arg Ala Leu Thr Ser Tyr Lys Asn Gln Ile Ala
Trp Arg Phe Ile Arg Ile Asn Ala Ala Cys Val Cys Val Leu Ser
Arg Asn Ser Trp Arg His or functional variants, analogues and functional fragments of NT-7.

The invention also provides the use of an essentially purified neurotrophin NT-7 having neurotrophic activity and an amino acid sequence SEQ ID NO.:1 as follows:

Lys Ala Asn Asp Phe Leu His Arg Gly Glu Tyr Ser Val Cys
Asp Ser Glu Glu His Trp Val Gly Asn Leu Thr Gln Ala Thr
Asp Leu Arg Gly Asn Glu Val Thr Val Leu Pro His Val Arg
Ile Asn Asn Val Val Lys Lys Gln Met Phe Tyr Glu Thr Thr
Cys Arg Val Ser Lys Pro Ile Gly Ala Pro Lys Pro Gly Gln
Gly Val Ser Gly Val Lys Ala Gly Thr Ser Ser Cys Arg Gly
Ile Asp Asn Glu His Trp Asn Ser Tyr Cys Thr Asn Val His
Thr Phe Val Arg Ala Leu Thr Ser Tyr Lys Asn Gln Ile Ala
Trp Arg Phe Ile Arg Ile Asn Ala Ala Cys Val Cys Val Leu Ser
Arg Asn Ser Trp Arg His or functional variants, analogues and functional fragments of NT-7 in the treatment of acute and/or chronic neuronal injury or degenerative states for a specific subclass of neurons.

The invention also provides the use of an essential purified neurotrophin NT-7 having neurotrophic activity and an amino acid sequence SEQ ID NO.:1 as follows:

Lys Ala Asn Asp Phe Leu His Arg Gly Glu Tyr Ser Val Cys
Asp Ser Glu Glu His Trp Val Gly Asn Leu Thr Gln Ala Thr
Asp Leu Arg Gly Asn Glu Val Thr Val Leu Pro His Val Arg
Ile Asn Asn Val Val Lys Lys Gln Met Phe Tyr Glu Thr Thr
Cys Arg Val Ser Lys Pro Ile Gly Ala Pro Lys Pro Gly Gln
Gly Val Ser Gly Val Lys Ala Gly Thr Ser Ser Cys Arg Gly
Ile Asp Asn Glu His Trp Asn Ser Tyr Cys Thr Asn Val His
Thr Phe Val Arg Ala Leu Thr Ser Tyr Lys Asn Gln Ile Ala
Trp Arg Phe Ile Arg Ile Asn Ala Ala Cys Val Cys Val Leu Ser
Arg Asn Ser Trp Arg His or functional variants, analogues and functional fragments of NT-7 in the identification of additional members of the neurotrophin family.

DETAILED DESCRIPTION OF THE INVENTION

The present invention relates to nucleic acid sequences encoding neurotrophin 7 (NT-7) as well as NT-7 protein, peptide fragments and derivatives produced using these nucleic acid sequences. In addition the invention relates to pharmaceutical compositions and therapeutic uses of NT-7.

The invention permits a comparison of the nucleic acid sequences of NT-7 and other neurotrophins.

Materials and Methods

1 Molecular Cloning of Xiphophorus NGF, NT-6, Carp NGF and NT-7

In an attempt to clone the carp NT-6, two exact oligonucleotides representing the amino acid sequence YSVCDS (GTACTCTGTGTGTGACAG) SEQ ID NO.: 3 & 4 and INAACV (CACACATGCAGCGTTGA) SEQ ID NO.:5 & 6, which corresponded to two conserved regions of NT-6, were designed. Carp genomic DNA (0.6 µg) was used in the polymerase chain reaction (PCR) as template. One-tenth of the reaction was further amplified by the same set of primers in a second PCR. The fragment was then gel purified and the ends were blunted by KLENOW™ (Amersham, UK) before being ligated to SmaI-cut pBLUESCRIPT™ (Stratagene, Calif.). After transformation into XL-1 BLUE™, the plasmid was purified and double-stranded DNA sequencing was performed (Sanger et al., 1977). The resulting fragment was designated as NT-7. Rapid amplification of cDNA ends (RACE) was employed in order to clone the full-length NT-7 from carp skin RNA. Methods were the same as stated in the protocol (GIBCO®, Life Technologies, NY). The 5'- and 3'-RACE revealed the sequence of part of the pre-pro region and the 3'-untranslated region. To clone the entire mature region, two primers (AAATGATACGGGGAGCC (SEQ ID NO.:7) and AAGGGGCGGAGTCTCAG (SEQ ID NO.:8)) located at the pre-pro and 3'-untranslated regions, respectively, were used to amplify NT-7 from 1.3 µg of carp genomic DNA using VENT™ polymerase (New England Biolabs, MA). The resulting fragment of 553 bp was subcloned into pBLUESCRIPT™ by blunt-end ligation as mentioned above. The partial sequence of carp NGF was amplified by PCR from 0.3 µg carp genomic DNA by a pair of degenerate primers that corresponded to the conserved regions FYETTC (SEQ ID NO.:13) and ACVCV (SEQ ID NO.:14). To clone the full-length Xiphophorus NGF and NT-6, two pairs or primers (CTTAGATCGTGTGCCCATG (SEQ ID NO.:9) and GGGTGAGTCTTCAATGCTG (SEQ ID NO.:10) for NGF; ATAACGTGGACGTGTGCCC (SEQ ID NO.:11) and CAAGAGCGGTCCACACCTC (SEQ ID NO.:12) for NT-6) were designed and PCR was performed using 1.8 µg Xiphophorus genomic DNA as template. The resulting products were subcloned into the expression vector pMT21. The cDNA sequence for carp NT-7 has been submitted to GENBANK™, with the Accession Number of U094949.

2 Southern Blot Analysis

Genomic DNA was prepared from 3 g of carp or Xiphophorus tissues as previously described (Ausubel et al., 1992). Genomic DNA (50 µg) was digested with 1500 units of HindIII for 6 hours, after which it was further digested by 980 units of the enzyme for 16 hours. Digested genomic DNA (16 µg) was loaded to each lane on 1% agarose gel. After being transferred to nylon membrane, it was hybridised at 50° C. in sodium phosphate buffer containing 25% formamide.

3 RNA Extraction, Northern Analysis, and RT-PCR

Selected tissues were dissected from adult carp and immediately frozen in liquid nitrogen. Total RNA was extracted from homogenized tissues by lithium chloride precipitation or guanidium thiocyanate extraction as described previously (Ip et al., 1995). Total RNA (15 µg) was electrophoresed on a 1% agarose-formaldehyde gel, transferred onto a nylon membrane (MSI, MA), and cross-linked by UV irradiation (Stratalinker, Stratagene, Calif.). A 340-bp fragment corresponding to the partial sequence of NT-7 was used as the probe for Northern analysis. The DNA fragment was gel purified by Qiaex (Qiagen, Germany) and labelled by random priming (Megaprime labelling kit, Amersham, UK). RNA blots were hybridised at 65° C. with radiolabelled probes in 0.5 M sodium phosphate buffer (pH 7), 1% bovine serum albumin, 7% SDS, 1 mM EDTA, and 20 µg/ml sonicated salmon sperm DNA. Filters were washed at 65° C. with 2×SSX, 0.1% SDS, and exposed to X-ray film (XAR-5, Kodak) with intensifying screens (Model SQZ-, C.B.S. Scientific CO., Inc.) at −80° C.

For RT-PCR analysis, 2 µg of RNA from various carp tissues was used as template in the reverse transcription that utilised SUPERSCRIPT RT™ (Gibco, N.Y.). The RNA was pretreated with 1 unit of RNase-free DNase (Promega, Wis.) for 30 minutes at 37° C. For the control, no RT was added and was substituted by DEPC—$H_2O$. One tenth of the reaction was amplified by two primers flanking the insertion. The resulting product was analysed in agarose gel and subjected to Southern blotting, using the same fragment used in the Northern blot analysis as probe.

4 Construction of Various Neurotrophins

A fusion protein that contained the pre-pro region of Xiphophorus NGF and mature region of NT-7 was constructed in order to test the activity of NT-7. The pre-pro region was amplified from the expression plasmid Xiphophorus NGF in pMT21 by sense primer located upstream of the XhoI cloning site of pMT21 and anti-sense primer that contained sequence at the end of the NGF pre-pro region plus 18 nucleotides from the beginning of the NT-7 mature region. The complementary sense primer and the antisense primer downstream of the NotI site of pBluescript were used to amplify the mature region of NT-7 (being subcloned into pBluescript). In a second PCR, the two fragments of DNA would anneal at the corresponding position because of the complementarity of the opposite ends, and the resulting NGF pre-pro/NT-7 chimera was amplified by the sense and antisense primers of pMT21 and pBluescript, respectively. The same approach was used to exchange the pre-pro region of NT-6.

To construct NT-7(D15) in which the 15-amino-acid insertion was deleted, a pair of complementary primers was designed which contained sequence immediately flanking the insertion. NT-7 (already fused with the NGF pre-pro region) encoded in pMT21 and pBluescript was used as template to produce the N- and C-terminal fragments, respectively. Because the two internal primers bypassed the insertion sequence, both the N- and C-terminal fragments did not contain the 15-amino-acid insertion. Using the two fragments as template in a second PCR (which involved sense and antisense primers of the two vectors) would geneate NT-7(D15). A similar approach was employed to construct NT-6 lacking the 22-amino-acid insert. Fc-tagged NGF, NT-6, and NT-6(D22) were constructed by fusing the human Fc sequence at the C-termini of the neurotrophins as previously described (Yang et al., 1997). All the different neurotrophin DNAs were subcloned in the expression vector pMT21 and transformed into DN10B.

5 Expression of Various Neurotrophins and Assay for Biological Activities

All the expression constructs were transfected into COS-5 cells using the diethylaminoethanol (DEAE)-dextran-chloroquine method as previously described (Lai et al., 1996), except that 5 µg of plasmid was used in each transfection, and the cells were maintained in Dulbecco's modified Eagle medium (DMEM) with 10% fetal bovine serum (FBS). Three days after transfection, the COS cell supernatant was collected and assayed for stimulation of neurite outgrowth from E8 chick DRG explants as described previously (Lindsay et al., 1985). The COS cell supernatant used in the assay was diluted 1:5 with DMEM+10% FBS. The DRG were fixed and stained after 1 day treatment by anti-neurofilament 160-kDa antibody (Clone NN18, Sigma, Mo.) as previously described (Ip et al., 1991). Similarly, the neurite-outgrowth activities of the Fc-tagged neurotrophins were determined except the COS cell supernatant that contained NGF-Fc was diluted 1:2.5 and the amount of NT-6 and NT-6(D22) was correspondingly adjusted by mock-transfected COS cell supernatant. The relative amount of the Fc-tagged neurotrophins in the COS cell supernatant was determined by ELISA as previously described (Ausubel et al., 1992), using anti-human Fc antibody (Amersham, UK). Based on the absorbance of the COS cell supernatant, the amounts of protein added to the cultures were equalised (equivalent to OD of 0.290±0.01 at 1:10 dilution, n=3, ±SEM).

To test whether the various neurotrophins could promote the survival of dissociated DRG neurons, the neurons were dissociated as previously described (Lindsay et al., 1985) and 3–4×$10^4$ cells (in DMEM+10% FBS) were plated onto 35-mm plate coated with 100 ng/ml poly-o-lysine, COS cell supernatant (1.2 ml) was added to each plate in a final volume of 2.2 ml (ie, the ratio of COS supernatant to medium was 6:5). The number of surviving neurons were counted after 20 hours.

6 Phosphorylation Assay of Trk Receptors in Fibroblasts

To test TrkA phosphorylation induced by the neurotrophins, 293 cells were transiently transfected by chick TrkA (Beckstrom et al., 1996) encoded in the expression vector pCDM8, and 2×$10^6$ cells were plated onto a 100-mm plate. Twenty-four hours later, the cells were transfected with 9 µg DNA in 8 ml Opti-minimal essential medium (Opti-MEM, Gibco, N.Y.) without penicillin/streptomycin but containing 40 µg lipofectamine (2 mg/ml, Gibco, N.Y.). The cells were incubated with the liposome-DNA mix for 5 hours at 37° C. before replaced by DMEM+10% FBS. The cells were refed at 20–24 hours after the start of transfection. Three days later, 2–3×$10^6$ cells were plated onto each 100-mm plate for phosphorylation assay. After 24 hours, the cells were starved in serum-free defined medium for 1 hour and then 2.5 ml of the COS cell supernatant (undiluted) was added to the cells and they were incubated for 5 minutes at 37° C. The cells were lysed by RIPA buffer and assayed for Trk receptor phosphorylation as previously described (Lai et al., 1996). Similar experiment was performed using 6:5 diluted COS cell supernatant. This served to show that NT-6(D22) and NGF/NT-6(D22) could still induce the weak TrkA phosphorylation under the same dilution utilised in the DRG survival assay. To assay TrkB and TrkC phosphorylation, 2×10⁶ chick fibroblasts stably transfected with full-length chick TrkB or TrkC were plated and the same procedure for TrkA phosphorylation was followed.

The invention will now be described by way of example only, with reference to the following Examples:

EXAMPLE 1

Molecular Cloning of Carp NT-7 and NGF

A DNA fragment of 340 bp was amplified from carp genomic DNA using primers corresponding to two conserved regions of NT-6. Subsequent cloning and DNA sequence analysis suggested the fragment might represent partial sequence of a novel neurotrophin. Northern blot analysis revealed its relatively strong expression in skin (see below). Therefore, in order to obtain the full-length sequence, 5'- and 3'-RACE (rapid amplification of cDNA ends) was performed using carp skin cDNA as template. The full-length clone which contained the putative translation start codon ATG and the signal peptide was not generated by the 5'-RACE. However, DNA sequence of the entire mature region could be obtained from the resulting clones. Subsequently, PCR using primers designed from sequence at the pre-pro and the 3'-untranslated region was performed to amplify the entire mature region.

DNA sequence analysis revealed that the pre-pro region was terminated at the two basic amino acids, arginine, followed by a mature region of 133 amino acids SEQ ID NO.:1. The R-X-K/R-R sequence was conserved in all neurotrophins and represented the proteolytic cleavage site, at which the mature protein was cleaved from its larger precursor (Hosaka et al., 1991). The presence of all 6 conserved cysteine residues together with the nearby conserved regions in the mature protein suggested that it represented a novel neurotrophin molecule. Amino acid alignment of this novel neurotrophin, designated NT-7, with that of Xiphophorus NGF and NT-6 revealed 66% identity. Moreover, alignment with carp BDNF, chick NT-3, and Xenopus NT-4 suggested even more distant relationships. However, NT-7 lacked some amino acid residues which were conserved in all NGF molecules identified so far.

Because of its structural similarity to NGF, it was possible that NT-7 merely represented the carp homologue of NGF. However, Southern blot analysis of carp genomic DNA revealed that different DNA fragments hybridised with Xiphophorus NGF and carp NT-7 (data not shown), suggesting that NGF and NT-7 represented different genes. To clone the carp NGF homologue, PCR was performed using several pairs of degenerate primers that corresponded to conserved regions near the cysteine residues. As a result, a 177-bp fragment was amplified from carp genomic DNA by one of the pairs of primers. Analysis of the deduced amino acid sequence indicated its close resemblance to NGF; it shared amino acid identity to the corresponding region of Xiphophorus NGF, carp NT-7, Xiphophorus NT-5, chick NT-3, carp BDNF, and Xenopus NT-4, respectively. In addition, it lacked those amino acid residues that were highly conserved in either BDNF, NT-3 or NT-4 of different species (Hallbook et al., 1991). These finding strongly suggested that this clone represented the partial sequence of carp NGF.

EXAMPLE 2

Southern Blot Analysis of Xiphophorus Genomic DNA

To examine whether NGF, NT-6 and NT-7 represent three different genes that coexist in one genome, Southern blot analysis of Xiphophorus genomic DNA, digested by HindIII, was performed and hybridised with Xiphophorus NF, NT-5, or carp NT-7 cDNAs under low stringency conditions. It was found that different patterns were obtained by hybridisation with the three neurotrophin cDNAs. The DNA fragments that hybridised with NGF were ~8 and ~3 kb, while a single fragment of ~8 and ~2 kb hybridised with NT-6 and NT-7, respectively. This suggested that NGF, NT-6, and NT-7 did represented three different genes.

EXAMPLE 3

Spatial Expression of NT-7 in Adult Carp

The spatial expression of NT-7 in adult carp was studied by Northern blot analysis. A single transcript of about 1.1 kb was detected in skin and heart, though weak expression was also found in brain and intestine. This was in contrast with that of NT-6, where expression in adult fish was predominantly found in brain, gill, liver, and eye, but not skin (Gotz et al., 1994).

Furthermore, the expression of NGF was studied in adult Xiphophorus in order to compare its spatial expression with that of NT-7. Northern blot analysis revealed dominant expression of a single transcript of ~3.6 kb in eye and gill, though weak expression could be detected in skin.

EXAMPLE 4

Presence of the 15-Amino-Acid Insertion in the NT-7 Transcript as Determined by RT-PCR One of the interesting features of NT-7 was the insertion of 15 amino acids between the second and third cysteine residues, a feature not found in any other known neurotrophins (including Xiphophorus NT-6 which contained an insertion of 22 amino acids at the corresponding position). The insertion contained only 4 glycine and 2 basic amino acid residues compared to the 8 glycine and 6 basic amino acid residues in Xiphophorus NT-6 that corresponded to the heparin-binding domain. In order to rule out the possibility of the insertion being an intron, RT-PCR was performed using a pair of primers flanking the insertion. All the tissues that were shown to express NT-7 in the Northern blot produced a single band which corresponded to the size having the insertion. Moreover, the band was absent when RT was performed using the same RNA samples but without reverse transcriptase. Thus, the resulting product which contained the insertion was not originated from contaminating genomic DNA, and there was no detectable alternative form of the NT-7 transcript that lacked the insertion.

EXAMPLE 5

Construction of NT-7 and Truncated NT-7 That Lacked the Insertion

Although the entire pre-pro region of NT-7 was not obtained, its biological activity could still be determined upon fusion of its mature region with the pre-pro portion of Xiphophorus NGF in order to express the protein. Moreover, it was reported that NT-6 might bind to cell surface through the heparin-binding domain, which would hinder its release into the conditioned medium after transfection. With the assumption that the 22 amino acids that corresponded to the heparin-binding domain are not essential in its biological activity, a truncated form of NT-6, named NT-6(D22), was constructed in which the 22 amino acid insertion was deleted in order to assay its neurotrophin activity in conditioned medium. Since NT-7 was expressed using the Xiphophorus NGF pre-pro region, two additional constructs of NT-6 and NT-6(D22), with pre-pro exchange, were made. Furthermore, the 15 amino acid insertion in NT-7 might lead to its binding to extracellular matrix, just like NT-6. Accordingly, a truncated form of NT-7 that lacked the 15-amino-acid insertion, NT-7(D15), was also constructed.

EXAMPLE 6

Biological Activities of NT-7

All the expression constructs were transiently transfected into COS-5 cells and conditioned medium was collected after 3 days. Neurite outgrowth assay of chick embryonic dorsal root ganglia (DRG) was employed to test the biological activities of the various neurotrophins. Addition of either Xiphophorus NGF or NT-7 resulted in robust neurite outgrowth from E8 DRG. Moreover, NT-7(D15) also showed comparable activity, suggesting that NT-7 was still active without the 15-amino-acid insertion. In contrast, the effect of either NT-6 or NT-6(D22) was similar to that obtained from conditioned medium of mock-transfected cells. Similar results were observed for the two NT-6 constructs with pre-pro exchange (data not shown). The neurotrophic activity of NT-7 was further investigated by the survival assay of dissociated DRG neurons. Consistent with the results of the neurite outgrowth assay, both NT-7 and NT-7(D15) could support the survival of E8 chick DRG neurons. On the other hand, NT-6 and NT-6(D22) failed to promote significant neuronal survival, irrespective of the pre-pro region. Thus, neurotrophic activity of NT-7 was demonstrated by its ability to stimulate neurite outgrowth and survival of DRG neurons, in a manner similar to that induced by Xiphophorus NGF.

EXAMPLE 7

Phosphorylation of TRK Receptors by NT-7

To elucidate its mechanism of action, the interaction between NT-7 and the various Trk receptors was studied by phosphorylation of different Trk receptors ectopically expression in fibroblasts. Because of its structural similarity to NGF, it would be expected that NT-7 showed receptor specificity to TrkA. Indeed, compared with the condition medium of mock-transfected COS cells, NT-7, NT-7(D15), and NT-6(D22) could weakly phosphorylate TrkA but not TrkB or TrkC. It should be noted that despite the relatively weak level of TrkA phosphorylation, it was consistently observed in triplicate experiments. The extent of TrkA phosphorylation elicited by NT-7, NT-7(D15), and NT-6 (D22) was considerably lower than that obtained by Xiphophorus NGF, NT-6(D22) failed to promote neurite outgrowth and survival of DRG, yet its induction of TrkA phosphorylation was similar to NT-7 and NT-7(D15). On the other hand, with the presence of the 22-amino-acid insertion, NT-6 was unable to stimulate any detectable level of TrkA phosphorylation, probably because of its binding to the cell surface or extracellular matrix, which subsequently hindered its release to the conditioned medium. Similarly, NT-6(D22) with NGF pre-pro region could induce weak TrkA phosphorylation (data not shown).

EXAMPLE 8

Construction of Fc-Tagged NGF and NT-6 and Assay for Neurite Outgrowth Activity

Since NT-6 had been demonstrated to promote the survival of chick DRG neurons (Gotz et al., 1994), the negative activity of NT-6 or NT-6(D22) in our study might be explained by lower expression and/or potency of the neurotrophin compared with NGF. To address this question, constructs of Xiphophorus NGF, NT6, and NT-6(D22) were tagged with the Fc region of human IgG. The relative amount of each neurotrophin in the conditioned medium was then determined by ELISA (see Experimental Methods), and their ability to stimulate neurite outgrowth of chick DRG was assayed after equalising the amount of each neurotrophin.

It was found that only NGF-Fc could stimulate the neurite outgrowth of DRG, while the activity of NT-6(D22)-Fc as well as NT-6-Fc (data not shown) was similar to that of conditioned medium of mock-transfected cells. Therefore, the different response of DRG to the two neurotrophins in our study was likely due to the lower potency of NT-6 in promoting neurite outgrowth. Indeed, the EC50 of purified NT-6 in supporting the survival of chick DRG was quite high (about 100 ng/ml; Gotz et al., 1994). It was therefore possible that the expression level of NT-6 and NT-6(D22) in our study was not high enough to reveal it activity on DRG neurons.

DISCUSSION

NT-6 was originally cloned from the aquarium fish Xiphophorus maculatus (Gotz et al., 1994), but so far no homologue in any other vertebrate was found. With the assumption that NT-6 was high homologous among different types of fish, particularly at the conserved regions around the cysteine residues, PCR was performed using a pair of primers at two conserved regions in order to clone the carp NT-6 homologue. It was therefore surprising that the resulting fragment, designated NT-7, only shared 66% amino acid identity to Xiphophorus NT-6. Apart from the relatively low percentage of homology, there was also considerable differences between the primary structure of the two neurotrophins. For example, the lack of an amino acid between Asn23 and Lys24, which was characteristic to NT-6 but not any other known neurotrophins, was found in NT-7. Moreover, the insertion present in NT-7 was considerably different from that of NT-6 in terms of the length and number of basic amino acid residues. Southern blot analysis demonstrated that NGF, NT-6, and NT-7 represented three different genes in the Xiphophorus genome. The partial sequence of carp NGF cloned in our study indicated that NGF and NT-7 were indeed two different genes. Since the homology between NGF and NT-7 is very similar to that between NT-7 and NT-6 (about 66% in both cases), it supports our claim that NT-7 represents a different gene from NT-6, rather than the carp NT-6 homologue. In addition, the spatial expression of NT-7 in adult tissues was quite different from that of Xiphophorus NGF and NT-6. In particular, high level of expression of NT-6 was reported in adult brain, eye, and gill, while NT-7 expression in the brain was low, and was even undetectable in eye and gill. Taken together, despite the relatively high evolutionary rate of neurotrophin in lower vertebrates (Gotz et al., 1992), NT-7 represents a novel member of the neurotrophin family.

In the present study, we have demonstrated the ability of NT-7 to stimulate neurite outgrowth and survival of E8 chick DRG. Unlike NT-7 and Xiphophorus NGF, NT-6 was unable to induce positive response from DRG in either assay. Although it has previously been suggested that the pre-pro region can affect the processing of mature neurotrophin (Ip et al., 1992), the pre-pro exchange with that of Xiphophorus NGF could not enable NT-6 to induce neurite outgrowth from DRG. It was possible that NT-6 secretion into the conditioned medium was hindered by its binding to cell surface or extracellular matrix, as suggested by Gotz et al (1994). However, NT-6(D22), which was expected to be released to the medium because of the absence of the heparin-binding domain, also could not activate the DRG in the neurite outgrowth and survival assay. Our assays using Fc-tagged NT-6(D22) suggested that NT-6 was less potent that NGF in stimulating neurite outgrowth of chick DRG. This finding is indeed consistent with the results obtained in two separate studies (Gotz et al., 1992, 1994), which suggested that NT-6 was much less potent than Xiphophorus NGF in promoting the survival of DRG: the concentration of Xiphophorus NGF causing half-maximal activity was 6 compared to 100 ng/ml of NT-6. It was possible that in our experiments, the concentration of the neurotrophin in COS cell supernatant was below the half-maximal value of NT-6 but not NGF, thus allowing for detectable response to NGF but not NT-6 in the DRG. Nonetheless, NT-6(D22) did exhibit the ability to induce weak TrkA phosphorylation.

Neurotrophins mediate their actions via phosphorylation of the Trk receptors. In our studies, the receptor specificity of NT-7 was determined by phosphorylation of chick Trks ectopically expressed in fibroblasts. As expected from the structural similarity to NGF, NT-7, NT-7(D15), and NT-6 (D22) specifically phosphorylated TrkA. However, the phosphorylation was considerably weaker than that induced by Xiphophorus NGF. The weaker phosphorylation of TrkA by NT-6(D22) or NGF NT-6(D22) was consistent with our hypothesis that NT-6 was less potent than Xiphophorus NGF in activating DRG neurons. However, NT-7 and NT-7(D15), despite their ability to activate DRG in both neurite outgrowth and survival assay, could only phosphorylate TrkA weakly. Indeed, the extent of TrkA phosphorylation was similar to that induced by NT-6(D22), which did not show any detectable activity on DRG in our studies. Both NT-7 and NT-7(D15) could not phosphorylate TrkB and TrkC, suggesting that the action on DRG was not mediated by these two Trk receptors. It remains possible that NT-7, but not NT-6, can activate a unique signalling pathway that mediates the response of DRG despite the modest activation of TrkA.

One important feature of NT-7 is the insertion of 15 amino acids at the position corresponding to the insertion of Xiphophorus NT-6. The insertion lacks the GT-AG sequence that is conserved in the intron/exon boundary. This, together with the result of RT-PCR, suggested that the insertion did not represent an intron. Since the activity of NT-7(D15) was as potent as NT-7 in both the DRG assay and the phosphorylation assay, the 15-amino-acid insertion was not indispensable in its biological activity. Its presence in the NT-7 molecule might be accessory to its neurotrophic function, such as binding to extracellular matrix which helped to localise the factor in the target area. If that is the case, it will be interesting to examine whether NT-7, like NT-6, binds to heparan sulfate or other types of molecules present in the extracellular matrix.

The cloning of this novel neurotrophin from carp shed new light on the diversity of neurotrophins in lower vertebrates. Considerably differences among NT-7, NGF, and NT-6 were observed in terms of primary structure and spatial expression. This, together with the Southern analysis of Xiphophorus genomic DNA and the low homology between NT-6 and NT-7 which is comparable with that of NGF, provide evidence that NT-7 is a novel neurotrophin.

What is claimed is:

1. An essentially purified neurotrophin of carp, carp NT-7 having neurotrophic activity and an amino acid sequence comprising SEQ ID NO. 1.

2. A composition of an essentially purified neurotrophin of carp, carp NT-7 having neurotrophic activity, comprising:
a carrier;
and an amino acid sequence comprising SEQ ID NO. 1.

* * * * *

SEQUENCE LISTING

```
<160> NUMBER OF SEQ ID NOS: 14

<210> SEQ ID NO 1
<211> LENGTH: 133
<212> TYPE: PRT
<213> ORGANISM: Cyprinus carpio

<400> SEQUENCE: 1

Lys Ala Asn Asp Phe Leu His Arg Gly Glu Tyr Ser Val Cys Asp Ser
1               5                   10                  15

Glu Glu His Trp Val Gly Asn Leu Thr Gln Ala Thr Asp Leu Arg Gly
            20                  25                  30

Asn Glu Val Thr Val Leu Pro His Val Arg Ile Asn Asn Val Val Lys
        35                  40                  45

Lys Gln Met Phe Tyr Glu Thr Thr Cys Arg Val Ser Lys Pro Ile Gly
    50                  55                  60

Ala Pro Lys Pro Gly Gln Gly Val Ser Gly Val Lys Ala Gly Thr Ser
65                  70                  75                  80

Ser Cys Arg Gly Ile Asp Asn Glu His Trp Asn Ser Tyr Cys Thr Asn
                85                  90                  95
```

-continued

```
Val His Thr Phe Val Arg Ala Leu Thr Ser Tyr Lys Asn Gln Ile Ala
            100                 105                 110
Trp Arg Phe Ile Arg Ile Asn Ala Ala Cys Val Cys Val Leu Ser Arg
        115                 120                 125
Asn Ser Trp Arg His
    130

<210> SEQ ID NO 2
<211> LENGTH: 519
<212> TYPE: DNA
<213> ORGANISM: Cyprinus carpio

<400> SEQUENCE: 2
ccaggcccgc gagtccggcg gaaggccaac gacttcttgc atcgcggcga gtactctgtg      60
tgtgacagcg aagagcactg ggttggcaac ctgacccaag ccacagactt acggggcaat     120
gaagtcacgg tgctgccaca tgttcgcatc aacaacgtgg tgaagaagca gatgttctac     180
gagaccacgt gccgtgtgtc gaagcccatc ggggccccca gccgggtca aggagtcagc      240 ggcgttaaag caggaacctc tagctgtcgt gggatcgaca acgagcactg gaactcttat     300
tgcaccaacg tgcacacctt tgtgcgggcg ttaacgtcct acaaaaacca gattgcctgg     360
aggttcatcc gaatcaacgc cgcttgcgtg tgcgtcctca ccgcaactc atggaggcat      420 tgactgacat attgtttcag ccaatccact gcagcctcct gtcgtaagcc cctcccaccc     480
atcaataata acaacagccg cactgccaac gttggtgat                            519

<210> SEQ ID NO 3
<211> LENGTH: 6
<212> TYPE: PRT
<213> ORGANISM: Artificial Sequence
<220> FEATURE:
<223> OTHER INFORMATION: Amino acid sequence for carp NT-6 primer

<400> SEQUENCE: 3

Tyr Ser Val Cys Asp Ser
1               5

<210> SEQ ID NO 4
<211> LENGTH: 18
<212> TYPE: DNA
<213> ORGANISM: Artificial Sequence
<220> FEATURE:
<223> OTHER INFORMATION: DNA primer for carp NT-6

<400> SEQUENCE: 4
gtactctgtg tgtgacag                                                    18

<210> SEQ ID NO 5
<211> LENGTH: 6
<212> TYPE: PRT
<213> ORGANISM: Artificial Sequence
<220> FEATURE:
<223> OTHER INFORMATION: Amino acid sequence for carp NT-6 primer

<400> SEQUENCE: 5

Ile Asn Ala Ala Cys Val
1               5

<210> SEQ ID NO 6
<211> LENGTH: 17
<212> TYPE: DNA
<213> ORGANISM: Artificial Sequence
```

```
<220> FEATURE:
<223> OTHER INFORMATION: DNA primer for carp NT-6

<400> SEQUENCE: 6
cacacatgca gcgttga                                                 17

<210> SEQ ID NO 7
<211> LENGTH: 17
<212> TYPE: DNA
<213> ORGANISM: Artificial Sequence
<220> FEATURE:
<223> OTHER INFORMATION: DNA primer for carp NT-7

<400> SEQUENCE: 7
aaatgatacg gggagcc                                                 17

<210> SEQ ID NO 8
<211> LENGTH: 17
<212> TYPE: DNA
<213> ORGANISM: Artificial Sequence
<220> FEATURE:
<223> OTHER INFORMATION: DNA primer for carp NT-7

<400> SEQUENCE: 8
aaggggcgga gtctcag                                                 17

<210> SEQ ID NO 9
<211> LENGTH: 19
<212> TYPE: DNA
<213> ORGANISM: Artificial Sequence
<220> FEATURE:
<223> OTHER INFORMATION: DNA primer for Xiphophorus NGF

<400> SEQUENCE: 9
cttagatcgt gtgcccatg                                               19

<210> SEQ ID NO 10
<211> LENGTH: 19
<212> TYPE: DNA
<213> ORGANISM: Artificial Sequence
<220> FEATURE:
<223> OTHER INFORMATION: DNA primer for Xiphophorus NGF

<400> SEQUENCE: 10
gggtgagtct tcaatgctg                                               19

<210> SEQ ID NO 11
<211> LENGTH: 19
<212> TYPE: DNA
<213> ORGANISM: Artificial Sequence
<220> FEATURE:
<223> OTHER INFORMATION: DNA primer for Xiphophorus NT-6

<400> SEQUENCE: 11
ataacgtgga cgtgtgccc                                               19

<210> SEQ ID NO 12
<211> LENGTH: 19
<212> TYPE: DNA
<213> ORGANISM: Artificial Sequence
<220> FEATURE:
<223> OTHER INFORMATION: DNA primer for Xiphophorus NT-6

<400> SEQUENCE: 12
caagagcggt ccacacctc                                               19
```

-continued

```
<210> SEQ ID NO 13
<211> LENGTH: 6
<212> TYPE: PRT
<213> ORGANISM: Artificial Sequence
<220> FEATURE:
<223> OTHER INFORMATION: Amino acid sequence for carp NGF primer

<400> SEQUENCE: 13

Phe Tyr Glu Thr Thr Cys
1               5

<210> SEQ ID NO 14
<211> LENGTH: 5
<212> TYPE: PRT
<213> ORGANISM: Artificial Sequence
<220> FEATURE:
<223> OTHER INFORMATION: Amino acid sequence for carp NGF primer

<400> SEQUENCE: 14

Ala Cys Val Cys Val
1               5
```